United States Patent [19]

Fehr et al.

[11] 4,195,086
[45] Mar. 25, 1980

[54] 6-BRANCHED CHAIN ALKYL SUSTITUTED ERGOT ALKALOIDS

[75] Inventors: Theodor Fehr, Dornach; Paul Stadler, Biel-Benke, both of Switzerland

[73] Assignee: Sandoz Ltd., Basel, Switzerland

[21] Appl. No.: 928,199

[22] Filed: Jul. 26, 1978

Related U.S. Application Data

[63] Continuation of Ser. No. 762,647, Jan. 26, 1977, abandoned, which is a continuation-in-part of Ser. No. 587,289, Jun. 16, 1975, abandoned.

[30] Foreign Application Priority Data

Jun. 21, 1974 [CH] Switzerland .................. 8533/74

[51] Int. Cl.² .................................. C07D 519/02
[52] U.S. Cl. .................................. 424/250; 544/346; 546/69
[58] Field of Search .................. 544/346; 424/250

[56] References Cited

U.S. PATENT DOCUMENTS

| 3,336,311 | 8/1967 | Hofmann et al. | 544/346 |
| 3,652,569 | 3/1972 | Stadler et al. | 544/346 |
| 3,920,664 | 11/1975 | Clemens et al. | 544/346 |

FOREIGN PATENT DOCUMENTS 769260  3/1957  United Kingdom ............ 260/285.5

OTHER PUBLICATIONS

Fehr et al., Helo. Chem. Acta. vol. 53, pp. 2197–2201, (1970).
Hofmann Die Nurtterkorn Alhodocill pp. 66–67, (1964).

*Primary Examiner*—Mary C. Lee
*Attorney, Agent, or Firm*—Gerald D. Sharkin; Robert S. Honor; Thomas O. McGovern

[57] ABSTRACT

This invention provides new compounds of formula I,

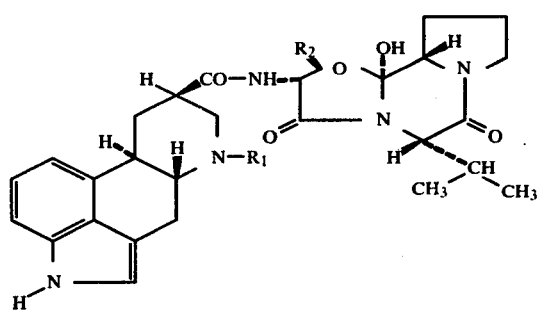

wherein
  $R_1$ is alkyl or 2 to 5 carbon atoms, and
  $R_2$ is methyl or ethyl,
useful as anti-migraine agents and for the treatment of orthostatic disorders.

18 Claims, No Drawings

6-BRANCHED CHAIN ALKYL SUSTITUTED ERGOT ALKALOIDS

This is a continuation, of application Ser. No. 762,647 filed Jan. 26, 1977, now abandoned, which in turn is a continuation-in-part of our application Ser. No. 587,289 of June 16, 1975 now abandoned.

The present invention relates to new heterocyclic compounds.

In accordance with the invention there are provided new compounds of formula I,

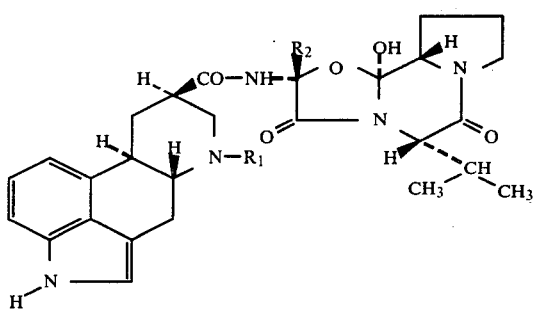

wherein
$R_1$ is alkyl of 2 to 5 carbon atoms, and
$R_2$ is methyl or ethyl.

Further, in accordance with the invention a compound of formula I may be obtained by a process comprising condensing a reactive functional derivative of an acid of formula II,

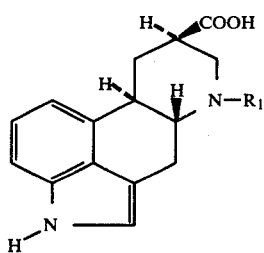

wherein
$R_1$ is as defined above, with a compound of formula III,

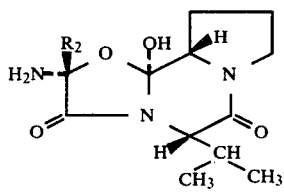

wherein
$R_2$ is as defined above, in acid addition salt form.
$R_1$ preferably is branched, especially in the α position to the nitrogen atom to which it is bound.

The reaction of the invention is a condensation reaction for amides. It may be carried out in a manner analogous to known methods.

The condensation is effected in an inert organic solvent or solvent mixture in the presence of an acid-binding agent.

For example, the condensation may be effected using as reactive functional derivative of an acid of formula II the addition product resulting from the reaction of an acid of formula II with a chlorinating agent and an N-di(lower)alkyl-substituted acid amide of an aliphatic carboxylic acid of 1 to 3 carbon atoms, such as dimethyl formamide or dimethyl acetamide. Other reactive derivatives of an acid of formula II, which may be produced in accordance with known methods, e.g. the acid chloride hydrochloride, the acid azide or mixed anhydrides of an acid of formula II with sulphuric acid or trifluoroacetic acid, may alternatively be used.

Suitable organic solvents are, for example, chloroform, methylene chloride, acetonitrile or dimethyl formamide, and suitable acid-binding agents are tertiary organic bases, e.g. pyridine or homologues thereof. Examples of chlorinating agents which may be used are thionyl chloride, phosgene or oxalyl chloride. The reaction may be effected at a temperature between $-30°$ and $0°$ C. and at normal pressure.

It is convenient to use 1.2 to 2.4 mols of an acid of formula II for every mol of a compound of formula III in salt form. The preferred salt form of the compounds of formula III is the hydrochloride. The course of the reaction is independent of the sequence of addition of the reagents.

The working up of the reaction mixture and isolation of the compounds of formula I may be effected in known manner.

Acid addition salt forms may be obtained in known manner from the free bases and vice versa. A suitable acid is tartaric acid.

The compounds of formula II, required as starting materials, are new and may be obtained in accordance with known methods. For example, a compound of formula IV,

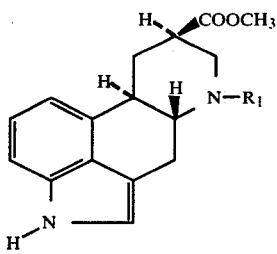

wherein
$R_1$ is as defined above, may be saponified under mild alkaline conditions, conveniently by treatment with caustic soda solution in an organic solvent or solvent mixture, and may then be weakly acidified.

The compounds of formula IV may be obtained by alkylation of 6-nor-9,10-dihydrolysergic acid methyl ester.

The compounds of formula III are known.

In the following non-limitative Examples all temperatures are indicated in degrees Centigrade and are uncorrected. Insofar as the production of the starting materials is not described, these are known or may be produced in accordance with known processes or in a manner analogous to known processes.

The name of the compounds of formula I is derived from the basic structure of formula V,

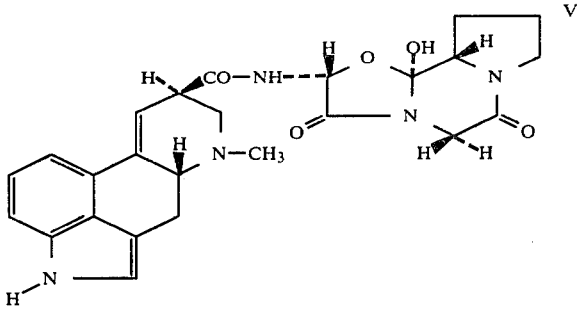

which is named ergopeptine for the sake of simplicity.

EXAMPLE 1

6-nor-6-isopropyl-9,10-dihydro-2'β-methyl-5'α-isopropyl-ergopeptine 8.6 cc of oxalyl chloride dissolved in 20 cc of acetonitrile are added dropwise, at $-10°$ to $-15°$, within 10 minutes to a solution of 300 cc of dimethyl formamide and 150 cc of acetonitrile, and stirring is effected for a further 10 minutes. 32 g of anhydrous 6-nor-6-isopropyl-9,10-dihydrolysergic acid are then sprinkled into the solution at $-20°$, and stirring is effected at $-10°$ for 30 minutes. After cooling to $-20°$ 200 cc of pyridine and 16.3 g of (2R,5S,10aS,10bS)-2-amino-2-methyl-5-isopropyl-3,6-dioxo-10b-hydroxyoctahydro-8H-oxazolo[3,2-a]pyrrolo[2,1-c]pyrazine hydrochloride are added, and stirring is effected at 0° for 2 hours. Working up is effected by adding 100 cc of a buffer solution pH=4 and distributing the reaction mixture between methylene chloride and a 2N soda solution. The organic phases are washed twice with water, dried with sodium sulphate and evaporated to dryness on a rotary evaporator. After drying in a high vacuum, the resulting crude base is dissolved in about 150 cc of ethanol and the solution is seeded. The title compound has an M.P. of 194° (decomp.), $[\alpha]_D^{20} = -32.3°$ (c=0.995 in methanol).

Production of the hydrogen tartrate form:

8.3 g of the base ($C_{31}H_{41}N_5O_5$) are dissolved in 120 cc of ethanol at about 50°, and 2.22 g of L-tartaric acid dissolved in about 10 cc of ethanol are added. After cooling to room temperature, the salt crystallizes. The precipitated salt is separated from the mother liquor, is washed with a small amount of ethanol and is then dried in a high vacuum at 80°. M.P. 200° (decomp.), $[\alpha]_D^{20} = -18.4°$ (c=1.0 in ethanol).

The 6-nor-6-isopropyl-9,10-dihydrolysergic acid, used as starting material, may, for example, be obtained by alkylation of 6-nor-9,10-dihydrolysergic acid methyl ester with isopropyl bromide and saponification of the resulting 6-nor-6-isopropyl-9,10-dihydrolysergic acid methyl ester (M.P. 194°).

6-nor-6-isopropyl-9,10-dihydrolysergic acid has an M.P. of 290° (decomp.), $[\alpha]_D^{20} = -101°$ (c=0.6 in methanol).

EXAMPLE 2

6-nor-6-isopropyl-9,10-dihydro-2'β-ethyl-5'α-isopropyl-ergopeptine

Production in a manner analogous to that described in Example 1. The title compound has an M.P. of 176°-178° (decomp.), $[\alpha]_D^{20} = -23°$ (c=0.5 in methylene chloride.

The compounds of formula I have not been described in the literature.

The compounds of formula I are useful because they possess pharmacological activity in animals. In particular, the compounds of formula I are useful as vasoconstrictor agents for the treatment of migraine and for the treatment of orthostatic disorders, e.g. circulatory disorders as indicated by standard tests, e.g. in the pithed rat test [Gillespie and Muir, Br. J. Pharmac. 30, 78–87 (1967)] on i.v. administration of from about 1 to about 10 μg/kg animal body weight, and in the Mellander-cat test [Angiologica 3, 77–99 (1966)] by an arterial vasotonic effect, on i.a. administration of from about 5 to about 45 μg/kg animal body weight.

For the above mentioned use the dosage will, of course, vary depending on the compound employed, mode of administration and therapy desired. However, in general, satisfactory results are obtained when administered at a daily dosage of from 1 μg to about 45 μg per kg animal body weight, conveniently given in divided doses 2 to 4 times a day or in sustained release form. For the larger mammal, the total daily dosage is in the range from about 0.1 to about 3 mg, and dosage forms suitable for oral administration comprise from about 0.02 mg to about 1.5 mg of the compounds admixed with a solid or liquid pharmaceutical carrier or diluent.

In a group of compounds $R_1$ is isopropyl and especially $R_2$ is methyl.

The compounds of formula I may be administered in pharmaceutically acceptable acid addition salt form. Such acid addition salt forms exhibit the same order of activity as the free base forms and are readily prepared in conventional manner. Representative acid addition salt forms include organic acid salt forms such as the hydrogen maleate, fumarate, tartrate and methane sulphonate and mineral acid salt forms such as the hydrochloride, hydrobromide and sulphate. A pharmaceutical composition may comprise a compound of formula I, in free base form or in pharmaceutically acceptable acid addition salt form, in association with a pharmaceutical carrier or diluent. Such compositions conveniently contain more than 1% by weight of the compound of formula I any may be prepared by conventional techniques to be in conventional forms, for example, capsules, tablets, suppositories, dispersible powders, syrups, elixirs, suspensions or solutions, for enteral or parenteral administration. Suitable pharmaceutical diluents or carriers include, for example, water, alcohols, natural or hardened oils and waxes, calcium and sodium carbonates, calcium phosphate, kaolin, talc and lactose as well as suitable preserving agents, such as ethyl-p-hydroxybenzoate, suspending agents such as methyl cellulose, tragacanth and sodium aliginate, wetting agents such as lecithin, polyoxyethylene stearate and polyoxyethylene sorbitan monooleate, granulating and disintergrating agents such as starch and alginic acid, binding agents such as starch, gelatin and acacia, and lubricating agents such as magnesium stearate, stearic acid and talc, in order to provide an elegant and palatable pharmaceutical preparation. Compositions in tablet form may be coated by conventional techniques to delay disintergration of the tablet and absorption of the active ingredient in the gastro-intestinal tract and thereby provide sustained action over a long period.

The preferred compositions from the standpoint of ease of administration are solid compositions, particularly solid-filled gelatin capsules and tablets.

We claim:

1. A compound of formula I,

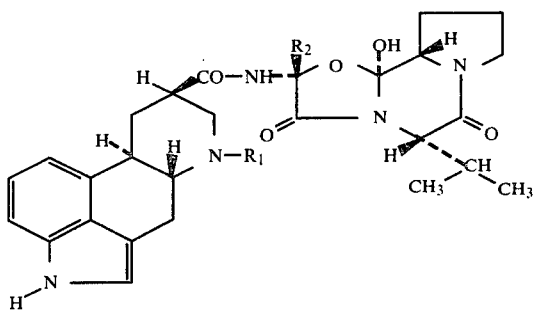

wherein
 $R_1$ is a branched chain alkyl of 3 to 5 carbon atoms, branched at the $\alpha$-position to the nitrogen to which it is bound, and
 $R_2$ is methyl or ethyl,
or a pharmaceutically acceptable acid addition salt thereof.

2. A compound of claim 1, wherein $R_1$ is isopropyl.

3. A compound of claim 1, wherein $R_2$ is methyl.

4. The compound of claim 1, which is 5-nor-6-isopropyl-9,10-dihydro-2'$\beta$-methyl-5'$\alpha$-isopropylergopeptine.

5. The compound of claim 1, which is 6-nor-6-isopropyl-9,10-dihydro-2'$\beta$-ethyl-5'$\alpha$-isopropylergopeptine.

6. A pharmaceutical composition useful in treating migraine comprising 0.1 to 3 milligrams of a compound of claim 1 in association with a pharmaceutical carrier or diluent.

7. The pharmaceutical composition of claim 6 in unit dosage form comprising from 0.02 to 1.5 milligrams of the said compound per unit dosage.

8. The pharmaceutical composition of claim 6 wherein, in the said compound, $R_1$ is isopropyl.

9. The pharmaceutical composition of claim 6 wherein, in the said compound, $R_2$ is methyl.

10. The pharmaceutical composition of claim 6 wherein the said compound is 5-nor-6-isopropyl-9,10-dihydro-2'$\beta$-methyl-5'$\alpha$-isopropyl-ergopeptine.

11. The pharmaceutical composition of claim 6 wherein the said compound is 6-nor-6-isopropyl-9,10-dihydro-2'$\beta$-ethyl-5'$\alpha$-isopropyl-ergopeptine.

12. A method of treating migraine in animals which comprises administrating to an animal in need of such treatment a therapeutically effective amount of a compound of claim 1.

13. The method of claim 12, wherein 0.1 to 3.0 milligrams of the said compound are administered daily.

14. The method of claim 13, wherein the dosage is administered in unit dosage form comprising 0.02 to 1.5 milligrams of the said compound.

15. The method of claim 12 wherein, in said compound, $R_1$ is isopropyl.

16. The method of claim 12 wherein, in said compound, $R_2$ is methyl.

17. The method of claim 12 wherein the said compound is 5-nor-6-isopropyl-9,10-dihydro-2'$\beta$-methyl-5'$\alpha$-isopropyl-ergopeptine.

18. The method of claim 12 wherein the said compound is 6-nor-6-isopropyl-9,10-dihydro-2'$\beta$-ethyl-5'$\alpha$-isopropyl-ergopeptine.

* * * * *